United States Patent
Chen et al.

(10) Patent No.: US 6,235,275 B1
(45) Date of Patent: May 22, 2001

(54) WATER-IN-OIL HAIR CONDITIONER WITH LAMELLAR DISPERSION IN WATER PHASE

(75) Inventors: Liang Bin Chen, Hoffman Estates; Wei-Mei Sun, Palatine, both of IL (US)

(73) Assignee: Unilever Home & Personal Care USA, a division of Conopco, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,015

(22) Filed: Jun. 25, 1999

(51) Int. Cl.$^7$ ............................. A61K 7/06; A61K 7/075; A61K 7/08
(52) U.S. Cl. ................. 424/70.1; 424/70.19; 424/70.27; 424/70.28; 424/401; 514/937
(58) Field of Search .................................. 424/401, 70.1, 424/70.19, 70.27, 70.28; 514/937

(56) References Cited

U.S. PATENT DOCUMENTS

| | | |
|---|---|---|
| 4,057,622 | 11/1977 | Hase et al. . |
| 4,784,844 | 11/1988 | Thimineur et al. . |
| 4,910,013 | * 3/1990 | Kanamaru et al. .................... 424/47 |
| 5,534,246 | 7/1996 | Herb et al. . |
| 5,539,021 | 7/1996 | Pate et al. . |
| 5,610,187 | * 3/1997 | Manning et al. ..................... 514/552 |
| 5,641,480 | * 6/1997 | Vermeer ............................ 424/70.24 |
| 5,658,557 | * 8/1997 | Bolich, Jr. et al. ............... 424/70.12 |
| 5,688,831 | 11/1997 | El-Nokaly et al. . |
| 5,753,216 | * 5/1998 | Leitch et al. ...................... 424/70.12 |
| 5,951,991 | * 9/1999 | Wagner et al. ....................... 424/401 |

FOREIGN PATENT DOCUMENTS

| | | |
|---|---|---|
| 0160430 | 11/1985 | (EP) . |
| 0435483 | 10/1994 | (EP) . |

* cited by examiner

Primary Examiner—Shelley A. Dodson
Assistant Examiner—Marina Lamm
(74) Attorney, Agent, or Firm—Matthew Boxer

(57) ABSTRACT

The invention relates to opaque hair conditioner compositions that have a lamellar dispersion in the internal aqueous phase and which are water in oil emulsions that comprise:

a) about 40 to 95% aqueous phase comprising (i) water and (ii) a cationic surfactant, capable of forming lamellar dispersion, present at about 0.1 to about 10% of the aqueous phase;

b) about 0.5 to about 30% oil, comprising a volatile silicone compound, a nonvolatile silicone compound, a volatile hydrocarbon compound, a nonvolatile hydrocarbon compound, or a mixture thereof;

c) about 0.1 to about 20% silicone surfactant; and d) optionally di-long chain alkyl amines having $C_{10}$ to $C_{22}$ carbon chains, long chain fatty alcohols having $C_{10}$ to $C_{22}$ carbon chains, or ethoxylated fatty alcohols.

22 Claims, No Drawings

WATER-IN-OIL HAIR CONDITIONER WITH LAMELLAR DISPERSION IN WATER PHASE

BACKGROUND OF THE INVENTION

Traditionally hair conditioners have used a combination of cationic surfactants and long chain fatty alcohols to provide a desirable viscosity and an opaque appearance. It is generally believed that the conditioning benefit is mainly due to the deposition of lamellar gel phase formed by a mixture of alkyl cationic quaternary ammonium compound and fatty alcohol. In most U.S. conditioners dialkyl cationic quat is used, whereas monoalkyl quat is used in most European formulations. The difference between these two systems is that the dialkyl quat can form a lamellar gel phase by itself while the monoquat is too water soluble to do so alone and requires the addition of fatty alcohol to create the lamellar gel structure.

Recent results suggest that to achieve the best instrumental wet combing for conditioners, less fatty alcohol is preferred. However, it is also known that taking fatty alcohol out of the dialkyl-based conditioners results in a translucent and thin product. These attributes are considered negatives by consumers. Therefore a problem in the art has been to thicken and opacify the non-fatty alcohol containing lamellar system. In the present invention, the compositions have both high viscosity and opacity through the use of a high internal phase water-in-oil emulsion with the lamellar gel particles dispersed inside the internal water phase.

The following is a list of patents in this field.

U.S. Pat. No. 4,057,622;
U.S. Pat. No. 5,539,021;
U.S. Pat. No. 5,534,246;
EP 0435483;
JP 10137576;
U.S. Pat. No. 5,688,831;
U.S. Pat. No. 4,784,844;
EP 160430;
JP 7165529;
Japanese Patent Application Kokai 3-193718 (published Aug. 23, 1991); and
JP 2068137

The present invention is directed to new opaque conditioning water in oil emulsion compositions that are esthetically acceptable to consumers, improve the wet combing and dry combing properties of hair, leave the dry hair with satisfactory cosmetic and physical properties. These compositions are easy to rinse, and leave the hair with a soft dry feel.

SUMMARY OF THE INVENTION

The invention relates to opaque hair conditioner compositions that have a lamellar dispersion in the internal aqueous phase.

The purpose of the invention is to provide a conditioner with improved performance, that is opaque and thick, and contains no fatty alcohol to thicken and opacify system.

More specifically, the present invention relates to opaque hair conditioner compositions which are water in oil emulsions which comprise a) about 40 to 95% aqueous phase comprising (i) water and (ii) a cationic surfactant, capable of forming lamellar dispersion, typically about 0.1 to about 10% of the aqueous phase b) about 0.5 to about 30% oil, comprising a volatile silicone compound, a nonvolatile silicone compound, a volatile hydrocarbon compound, a nonvolatile hydrocarbon compound, or a mixture thereof.

c) about 0.1 to about 20% silicone surfactant.

d) optional compounds are those compounds that cannot form a lamellar phase alone, but can participate in the formation of a lamellar phase in the presence of cationic surfactants, in a amount of 0 to about 10%, and preferably about 0.1 to 5% by weight of the aqueous phase. Exemplary classes of such compounds includes di-long chain alkyl amines (i.e. $C_{10}$ to $C_{22}$), long chain fatty alcohols (i.e. $C_{10}$ to $C_{22}$), ethoxylated fatty alcohols.

The cationic surfactant is present at a most preferred range of about 1 to about 5% of the aqueous phase.

The aqueous phase is present in a range of about 70 to about 92%, most preferably at about 75 to about 90%.

Component b is present at about 3 to about 20% of the aqueous phase, most preferably at about 5 to about 15% of the aqueous phase.

The silicone surfactant is present preferably at about 0.1–15% of the aqueous phase, most preferably at about 0.1–10% of the aqueous phase.

The compositions of the invention have the following viscosity ranges measured at 80° F.: using Brookfield at T-spindle (TA or TB) at 0.5 rpm 20,000 cps to 600,000 cps; RV 4 to 6 spindle, 20 rpm, 100 cps to 20,000 cps.

Most preferably, the present invention relates to opaque hair conditioner compositions which are water in oil emulsions which comprise:

a) about 1 to about 6% cationic surfactant in the aqueous phase b) about 0 to about 10% silicone oil or about 0 to about 10% hydrocarbon oil with the proviso that the silicone oil and the hydrocarbon oil cannot both be 0.

c) about 0.4 to about 7% silicone surfactant

The oil phase of these compositions comprises ingredients b and c. The aqueous phase comprises ingredient a.

As noted above, in the present invention, the compositions have both high viscosity and opacity through the use of a high internal phase water-in-oil emulsion with the lamellar gel particles dispersed inside the internal water phase. These compositions deliver lamellar gel phase onto the hair.

Another aspect of the invention is to provide a method of treating the hair to yield well-conditioned hair having esthetically pleasing physical properties by contacting the hair with an opaque conditioner of the present invention.

Another aspect of the invention is to provide a conditioning composition which is easy to rinse from the hair. The compositions of the invention are easy to rinse from the hair due to the presence of the lamellar dispersion.

DETAILED DESCRIPTION OF THE INVENTION

Unless indicated otherwise, as used herein, % means weight %. The starting materials set forth herein are either known or can be prepared in accordance with known methods.

By the word lamellar is meant lyotropic lamellar phases. The lamellar phases including lamellar dispersion consist of stacks of surfactant bilayers separated by a solvent, usually water. The non-polar portions of the surfactant associate with each other and form a bilayer unit. Water is dispersed between the layers of surfactant polar groups. In this invention, the lamellar phase consists of a multilayered vesicle (or liposome)-like structure at ambient temperature. That is, the surfactant systems used in this invention have a Krafft temperature higher than 25° C. The Krafft temperature corresponds to the melting point of the hydrocarbon chains in the surfactant, and is the temperature below which the surfactant hydrocarbon chains are solid-like and ordered. For example, the Krafft temperature for the distearyldimethylammonium chloride is about 47° C. Below that temperature including room temperature the surfactants form lamellar dispersed phases with particle sizes in the ranges of sub-micron to ten microns.

More specifically, the present invention relates to opaque hair conditioner compositions which are water in oil emulsions which comprise
  a) about 40 to 95% aqueous phase comprising (i) water and (ii) a cationic surfactant, capable of forming lamellar dispersion, typically about 0.1 to about 10% of the aqueous phase
  b) about 0.5 to about 30% oil, comprising a volatile silicone compound, a nonvolatile silicone compound, a volatile hydrocarbon compound, a nonvolatile hydrocarbon compound, or a mixture thereof.
  c) about 0.1 to about 20% silicone surfactant.
  d) optional compounds are those compounds that cannot form a lamellar phase alone, but can participate in the formation of a lamellar phase in the presence of cationic surfactants, in a amount of 0 to about 10%, and preferably about 0.1 to 5% by weight of the aqueous phase. Exemplary classes of such compounds includes di-long chain alkyl amines (i.e. $C_{10}$ to $C_{22}$), long chain fatty alcohols (i.e. $C_{10}$ to $C_{22}$), ethoxylated fatty alcohols.

The cationic surfactant is present at a most preferred range of about 1 to about 5% of the aqueous phase.

The aqueous phase is present in a range of about 70 to about 92%, most preferably at about 75 to about 90%.

Component b is present at about 3 to about 20% of the aqueous phase, most preferably at about 5 to about 15% of the aqueous phase.

The silicone surfactant is present preferably at about 0.1–15% of the aqueous phase, most preferably at about 0.1–10% of the aqueous phase.

Most preferably, the present invention relates to opaque hair conditioner compositions which are water in oil emulsions which comprise:
  a) about 1 to about 6% cationic surfactant in the aqueous phase
  b) about 0 to about 10% silicone oil or about 0 to about 10% hydrocarbon oil with the proviso that the silicone oil and the hydrocarbon oil cannot both be 0.
  c) about 0.4 to about 7% silicone surfactant The oil phase of these compositions comprises ingredients b and c. The aqueous phase comprises ingredient a.

As noted above, in the present invention, the compositions have both high viscosity and opacity through the use of a high internal phase water-in-oil emulsion with the lamellar gel particles dispersed inside the internal water phase. These compositions deliver lamellar gel phase onto the hair.

Another aspect of the invention is to provide a method of treating the hair to yield well-conditioned hair having esthetically pleasing physical properties by contacting the hair with an opaque conditioner of the present invention.

Another aspect of the invention is to provide a conditioning composition which is easy to rinse from the hair. The compositions of the invention are easy to rinse from the hair due to the presence of the lamellar Cationic surfactants in the compositions of the invention can have the structure

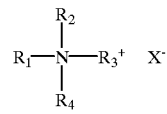

wherein $R_1$ is an alkyl group including from about 8 to about 20 carbon atoms; $R_2$ is selected from the group consisting of an alkyl group including from about 8 to about 20 carbon atoms, a hydrogen atom, a methyl group, an ethyl group, a hydroxymethyl group and a hydroxyethyl group; $R_3$ is selected from the group consisting of a benzyl group, a hydrogen group, a methyl group, an ethyl group, a hydroxymethyl group and a hydroxyethyl group; $R_4$ is selected from the group consisting of a hydrogen atom, a methyl group, an ethyl group, a hydroxymethyl group and a hydroxyethyl group; and x is an anion. The quaternary nitrogen of the water-soluble quaternary ammonium compound also can be a component of a heterocyclic nitrogen-containing moiety, such as morpholine or pyridine. The anion of the quaternary ammonium compound can be any common anion, such as chloride, methosulfate, ethosulfate, nitrate, bromide, tosylate, acetate, or phosphate.

The water-soluble quaternary ammonium compounds have one or two long chain alkyl groups containing from about 8 to about 18 carbon atoms. The long chain alkyl groups also can include, in addition to, or in replacement of, carbon and hydrogen atoms, ether linkages or similar water-solublizing linkages. The remaining two or three substitutes of the quaternary nitrogen of the quaternary ammonium compound can be hydrogen; benzyl; or short chain alkyl or hydroxyalkyl groups, such as methyl, ethyl, hydroxymethyl or hydroxyethyl groups; or combinations thereof, either of the same or different identity.

Exemplary water-soluble quaternary ammonium compounds include, but are not limited to, laurtrimonium chloride; Quaternium-16; lauralkonium chloride; olealkonium chloride; dilauryidimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; polyquaternium-11; polyquaternium-5; polyquaternium-10; polyquaternium-24; cetrimonium chloride; Quaternium-24; mytrimonium chloride; PEG-2 cocomonium chloride; PEG-2 cocoyl quaternium 4; PEG-15 cocoyl quaternium 4; PEG-2 stearyl quaternium 4; PEG-15 stearyl quaternium 4; PEG-2 oleyl quaternium 4; PEG-15 oleyl quaternium 4, and mixtures thereof, wherein the compound designation is provided by the Cosmetic, toiletry and Fragrance Association, Inc. in the CTFA Cosmetic Ingredient Dictionary, 4th Ed., 1991, hereinafter referred to as the CTFA Dictionary, Other water-soluble quaternary ammonium compounds are listed in the CTFA Cosmetic Ingredient Handbook, 1st Ed., 1988 (hereinafter the CTFA Handbook) at page 40–42, incorporated herein by reference.

Exemplary of the silicone surfactants or emulsifiers that are used in compositions of the invention is a dimethicone, which is a dimethylsiloxane polymer having polyoxyethylene and/or polyoxypropylene side chains, such as DOW CORNING 3225C and 5225C FORMULATION AID, available from Dow Corning Co., Midland, Mich., ABIL EM 97, available from Goldschmidt Chemical Corporation, Hopewell, Va. and SILWET™ series, available from OSI Specialties, Inc., Danbury, Conn. The dimethicone copolyol has about 15 or fewer ethylene oxide and/or propylene oxide monomer units, in total, in the side chains. Dimethicone copolyols conventionally are used in conjunction with silicones because the oil-soluble, silicon-based surfactants are extremely soluble in a volatile or a nonvolatile silicone compound, are extremely insoluble in water.

These dimethicone copolyols which are employed in compositions of the invention, can be dimethicone copolyols with HLB values of less than 10, more preferably about 2 to about 8. These dimethicone copolyols can have a molecular weight of about 600 to about 20,000. These dimethicone copolyols can be from the SILWET series such as DC 5225C and DC 3225C. Also alkyl dimethicones such as cetyl dimethicone can be used in compositions of the invention.

Dimethicone copolyols can have the following formula:

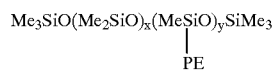

Wherein

Wherein Me is methyl, EO is ethyleneoxy, PO is 1,2-propyleneoxy, x and y are 1 or greater, m and n are 0 or greater, provided that the molecular weight of the PE moiety must be greater than 1,000 and Z is hydrogen or lower alkyl (like a $C_1$–$C_5$ alkyl).

Another exemplary, but non-limiting, oil-soluble, silicon-based surfactant is an alkyl dimethicone copolyol, such as cetyl dimethicone copolyol available commercially as ABIL²?EM 90 from Goldschmidt Chemical Corporation, Hopewell, Va. the alkyl dimethicone copolyols have the structure:

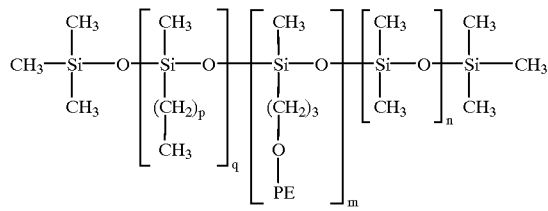

wherein p is numeral from 7 through 17;

q is a numeral from 1 through 100;

m is a numeral from 1 through 40;

n is a numeral from 0 through 200; and

PE is $(C_2H_4O)_a(C_3H_6O)_b$—H having a molecular weight of about 250 to about 2000, wherein a and b are selected such that the weight ration of $C_2H_4O/C_3H_6O$ is from 100/0 to 20/80.

Structure of Volatile Silicone Oils which can be Included in Compositions of the Invention The silicone oil phase of the compositions of the invention comprises a volatile silicone oil, a nonvolatile silicone oil phase or a mixture thereof preferably, the volatile silicone compound. Exemplary volatile silicone compounds include, but are not limited to, volatile, low molecular weight polydimethylsiloxane compounds. They can be either a linear or a cyclic polydimethylsiloxane compound having a viscosity of about 0.5 to 10 cst (centistokes). The preferred volatile polydimethylsiloxanes have a viscosity in the range of about 0.5 to about 6 cst.

The cyclic, volatile, low molecular weight polydimethylsiloxanes, designated in the *CTFA Dictionary* as cyclomethicones, are the preferred siloxanes used in a composition of the present invention. These volatile compounds have an average of about 3 to about 6-[O—Si $(CH_3)_2$] - repeating group units per molecule (hexamethylcyclotrisiloxane, octamethylcyclotetrasiloxane, decamethylcyclopentasiloxane, dodecamethylcyclohexasiloxane, and mixtures thereof); boil at atmosphere pressure at about 150° C. to about 250° C. The polydimethyl cyclosiloxanes having an average of about 4 to about 5 repeating units per molecule are especially preferred. Suitable cyclomethicones are available commercially under the trade names DOW CORNING 245 Fluid, DOW CORNING 344 Fluid and DOW CORNING 345 Fluid from DOW CORNING Corporation, Midland, Mich., and SILICONE SF-1 173 and SILICONE SF-1202 from General Electric, Waterford, N.Y.

An example of a linear, low molecular weight, volatile polydimethylsiloxane compound is designated in the *CTFA Dictionary* as decamethyltetrasiloxane, available commercially under the trade names DOW CORNING 200 Fluid having a viscosity of 1.5 cst and a boiling point of 195° C. Other linear polydimethylsiloxanes includes octamethyltrisiloxane, and decamethylpentasiloxane also be useful in the composition of the present invention.

Structure of Volatile Hydrocarbon Oils which can be included in Compositions of the Invention The volatile hydrocarbon oil phase comprises about 6 to 20 carbon atoms. A preferred volatile hydrocarbon compound is an aliphatic hydrocarbon having about 8 to 16 carbon atoms, and having a boiling point of about 100 to 250° C. Exemplary volatile hydrocarbon compound include, isododecane and isohexadecane, i.e., PERMETHYL 99A, PERMETHYL 101A, available from Presperse, Inc., South Plainfield, N.J. Other examples are depicted in general structure formula (I), wherein n ranges from 2 to 3.

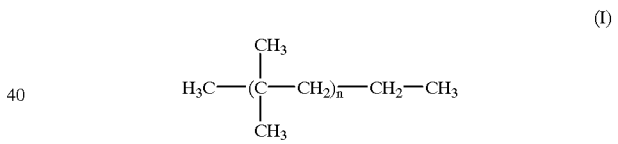

(I)

Another exemplary volatile hydrocarbon compound is ISOPAR M (a $C_{12}$–$C_{14}$ isoparaffin available From EXXON Chemical Co., Baytown, Tex.).

Structure of Non-volatile Silicone Compounds which can be included in Compositions of the Invention Exemplary nonvolatile silicone compounds include a polydimethylsiloxane, polyalkyl siloxane, a polyaryl siloxane or a polyalkylaryl siloxane. The nonvolatile silicones are nonfunctional siloxanes or siloxane mixtures having a viscosity of about 10 to about 10,000 cst, and most preferred viscosity about 10 to 500 cst at 25° C. A nonvolatile silicone compound having a boiling point at atmospheric pressure of greater than about 250° C. A phenyltrimethicone also is useful as a nonvolatile silicone compound. Example include DC 556 fluid, which is available from Dow Corning.

Structure of Non-volatile Hydrocarbon Compounds which can be included in Compositions of the Invention The nonvolatile oil phase also can comprise a nonvolatile hydrocarbon compound, such as mineral oil, isoeicosane. Other exemplary compounds includes water insoluble emollient, such as, for example, an ester having at least about 10 carbon atoms, and preferably about 10 to about 32 carbon atoms. Suitable esters include but not limited to, for example, aliphatic monohydric alcohol esters including isopropyl myristate and aliphatic di- or tri-esters of polycarboxylic acids including dioctyl adipate.

Examples of Optional Compounds which can be included in Compositions of the Invention Exemplary classes of such compounds includes di-long chain alkyl amines (i.e. $C_{10}$ to $C_{22}$), long chain fatty amine (i.e. $C_{10}$ to $C_{22}$), long chain fatty alcohols (i.e. $C_{10}$ to $C_{22}$), ethoxylated fatty alcohols, and double-tailed phospholipids. Specific compounds capable of participating in the formation of a lamellar dispersed phase, include dipalmitylamine, stearamidopropyldimethylamine, cetyl alcohol, stearyl alcohol, steareth-2, steareth-21, phosphatidylserine, phosphatidyicholine and mixtures thereof.

Other optional ingredients included in compositions of the invention may be paraffin, vaseline solid paraffin, squalene, oligomer olefins and the like; amidoamines such as stearamidopropyl dimethylamine, isostearamidoethyl morpholine, behenamidopropyl dimethylamine and the like; humectants such as glycerine, propylene glycol, glycerol, sorbitol and the like; esters, such as isopropyl palmitate, isopropyl myristate, and stearyl stearate and the like; emulsifiers such as glyceryl monostearate, sorbitan monopalmitate, polyoxyethylene stearate and the like; cellulose derivatives such as hydroxypropylcellulose; cationic cellulose, hydroxyethyl cellulose and the like; thickening agents such as natural polymers and the like; and other ingredients such as solvents, bacteriocides, colors, and fragrances.

Compositions of the invention can take the form of leave-in or rinse out conditioners.

Compositions of the invention may be prepared by methods which are known to those skilled in the art. Ingredients used in the preparation of compositions of the invention are either known or may be prepared by known methods.

To use the rinse out compositions of the invention to condition hair, one first wets the hair, then applies the composition of the invention, then lathers the hair, and then rinses the hair. Alternatively, water and conditioner may be applied to the hair simultaneously. Conditioning with compositions may be done right after shampooing when the hair is still wet. Alternatively, conditioning the hair may be done separately from shampooing.

Compositions of the invention may be leave-in conditioners as mentioned above. In such cases, the compositions of the invention are simply worked into the hair usually by using the fingers.

Compositions of the invention provide unexpectedly superior conditioning without the use of fatty alcohols.

Compositions of the invention can be prepared as follows:

1) Prepare lamellar phase dispersion with cationic surfactant and water. Heating can accompany this step.
2) Premix the oil phase with the silicone surfactants.
3) Emulsify 1 and 2.

To demonstrate the new and unexpected results achieved by the present invention, the compositions of the invention as shown below were prepared. These compositions were prepared using known starting materials or starting materials which may be obtained by known methods. These compositions were prepared by methods which are known in the art or which are analogous to those known in the art.

The compositions of the invention are as follows:

Example of High Internal Phase Emulsion using Different Types of Silicone Emulsifiers

| Formulation | A | B | C | D |
|---|---|---|---|---|
| Oil Phase | | | | |
| Abil EM 90[1] | 4 | | | |
| Abil EM 97[2] | | 5 | | |
| Silwet 7622[3] | | | 5 | |
| Amersil ME-358[4] | | | | 2 |
| Cyclomethicone, DC245 | 11 | 13 | | 4.2 |
| Cyclomethicone, DC244 | | | 15 | |
| Aqueous Phase | | | | |
| Water | 83 | 80 | 78.5 | 92 |
| Varisoft TA-100[5] | 2 | 2 | 1.5 | 1.8 |

[1]Cetyl Dimethicone copolyol, 100% active, from Goldschmidt
[2]Dimethicone Copolyol and Cyclopentasiloxane, 85% active, from Goldschmidt
[3]Dimethicone Copolyol, 100% active, from OSI Specialties
[4]Cyclomethicone and Dimethicone Copolyol, 10% active, from Amerchol, Edison, NJ.
[5]Distearyldimethylammonium Chloride, 100% active, from Witco Corp., Greenwich, CT.

The following are examples of high internal phase emulsions using different types of non-volatile external oils.

| Formulation | A | B | C | D | E |
|---|---|---|---|---|---|
| Oil Phase | | | | | |
| Abil EM 90 | 3 | 4.5 | 3.2 | 4 | 4 |
| DC556 Silicone Fluid[6] | 14 | | | | |
| Light Mineral Oil | | 13.5 | | | |
| Isopropylpalmitate | | | 7 | | |
| Dioctyl adipate | | | | 10.3 | |
| Hexyl trimethicone | | | | | 8 |
| Aqueous Phase | | | | | |
| Water | 81 | 80.5 | 88 | 84 | 86.1 |
| Varisoft TA-100[5] | 2 | 1.5 | 1.8 | 1.7 | 1.9 |

[6]Polyphenylmethylsioxane, nonovolatile silicone oil, 100% active, from Dow Corning.

Examples of Wet-Combing Force Data for Different Formulations

Generally, the lower the wet combing force the better the wet conditioning. Conventional conditioners have a wet combing force that ranges from about 10 to about 20 gm.

Wet combing experiments were carried out on the Instron 5500 series. All testing was carried out by applying 0.3 mL of product to bleached and waved 2 gm hair tresses.

| Formulation | C | D | E |
|---|---|---|---|
| Oil Phase | | | |
| DC 3225C | | 7 | 7 |
| DC 200, 5 cst | | 3 | 3 |
| Fragrance | | 0.25 | 0.25 |
| Aqueous Phase | | | |
| Water | 92.6 | 85.45 | 83.45 |
| Varisoft 432 PPG (30% Dicetyldimonium Chloride) | 7 | | 6 |
| NaCl | | 4 | |
| Preservative | 0.4 | 0.3 | 0.3 |
| Total | 100 | 100 | 100 |
| Combing force (gm force) | 9.9 | 21.6 | 7.9 |

| Formulation | F | G | H | I | J | K |
|---|---|---|---|---|---|---|
| | Weight percent | weight percent | weight percent | weight percent | weight percent | weight percent |

-continued

| Oil Phase | | | | | | |
|---|---|---|---|---|---|---|
| DC 5225C | 5 | 5 | 5 | 7 | 5 | 5 |
| DC 200, 5 cst | 3 | 3 | 3 | 3 | | |
| DC 200, 1.5 cst | 2 | 2 | 2 | | | |
| DC 245 | | | | 5 | | |
| Permethyl 101A | | | | | | 5 |
| Fragrance | 0.25 | 0.25 | 0.25 | 0.25 | 0.25 | 0.25 |
| Aqueous Phase | | | | | | |
| soft water | 83.45 | 85.25 | 84.45 | 84.45 | 85.25 | 85.25 |
| Varisoft 432 PG (30% dicetyl-dimonium chloride) | 6 | | | | | |
| Distearyl-dimonium chloride | 0 | 4.2 | 5 | 5 | 4.2 | 4.2 |
| Preservative | 0.3 | 0.3 | 0.3 | 0.3 | 0.3 | 0.3 |
| Total | 100 | 100 | 100 | 100 | 100 | 100 |
| Combing force (gm force) | 9.7 | 8.9 | 8.0 | 7.9 | 9.0 | 10.3 |

Compositions of the invention showed equal or better wet-combing force than a commercial composition.

What is claimed is:

1. An opaque water in oil hair conditioning composition comprising:
    a) about 40 to 95% aqueous phase comprising (i) water and (ii) a cationic surfactant, capable of forming lamellar dispersion, said cationic surfactant being present at about 0.1 to about 10% of the aqueous phase;
    b) about 0.5 to about 30% oil, comprising a volatile silicone compound, a nonvolatile silicone compound, a volatile hydrocarbon compound, a nonvolatile hydrocarbon compound, or a mixture thereof;
    c) about 0.1 to about 20% silicone surfactant; and
    d) optionally di-long chain alkyl amines having $C_{10}$ to $C_{22}$ carbon chains, long chain fatty alcohols having $C_{10}$ to $C_{22}$ carbon chains, or ethoxylated fatty alcohols, wherein the internal aqueous phase contains lamellar gel particles dispersed therein.

2. A composition in accordance with claim 1 wherein the cationic surfactant is present at range of about 1 to about 5% of the aqueous phase.

3. A composition in accordance with claim 1 wherein the aqueous phase is present in a range of about 70 to about 92%.

4. A composition in accordance with claim 1 wherein the aqueous phase is present in a range of about 75 to about 90%.

5. A composition in accordance with claim 1 wherein component b is present at about 3 to about 20% of the aqueous phase.

6. A composition in accordance with claim 1 wherein component b is present at about 5 to about 15% of the aqueous phase.

7. A composition in accordance with claim 1 wherein the silicone surfactant is present at about 0.1–15% of the aqueous phase.

8. A composition in accordance with claim 1 wherein the silicone surfactant is present at about 0.1–10% of the aqueous phase.

9. A composition in accordance with claim 1 which comprises:
    a) about 1 to about 6% cationic surfactant in the aqueous phase
    b) about 0 to about 1 0% silicone oil or about 0 to about 10% hydrocarbon oil with the proviso that the silicone oil and the hydrocarbon oil cannot both be 0.
    c) about 0.4 to about 7% silicone surfactant.

10. A composition according to claim 1 which is a rinse out conditioner.

11. A composition according to claim 1 which is a leave-in conditioner.

12. A composition according to claim 1 wherein the cationic surfactant is a compound of the formula

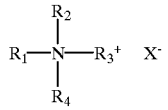

wherein $R_1$ is an alkyl group including from about 8 to about 20 carbon atoms; $R_2$ is selected from the group consisting of an alkyl group including from about 8 to about 20 carbon atoms, a hydrogen atom, a methyl group, an ethyl group, a hydroxymethyl group and a hydroxyethyl group; $R_3$ is selected from the group consisting of a benzyl group, a hydrogen group, a methyl group, an ethyl group, a hydroxymethyl group and a hydroxyethyl group; $R_4$ is selected from the group consisting of a hydrogen atom, a methyl group, an ethyl group, a hydroxymethyl group and a hydroxyethyl group;

or the quaternary nitrogen of the water-soluble quaternary ammonium compound is a component of the heterocyclic nitrogen-containing moiety, morpholine or pyridine and the anion of the quaternary ammonium compound is chloride, methosulfate, ethosulfate, nitrate, bromide, tosylate, acetate, or phosphate.

13. A composition according to claim 12 wherein the cationic surfactant compound has one or two long chain alkyl groups containing from about 8 to about 18 carbon atoms which can include, in addition to, or in replacement of, carbon and hydrogen atoms, ether linkages or similar water-solublizing linkages and wherein the remaining two or three substitutes of the quaternary nitrogen of the quaternary ammonium compound can be hydrogen; benzyl; or short chain alkyl or hydroxyalkyl groups, selected from the group consisting of methyl, ethyl, hydroxymethyl, hydroxyethyl groups; and combinations thereof, either of the same or different identity.

14. A composition according to claim 12 wherein the cationic surfactant is selected from the group consisting of laurtrimonium chloride; Quaternium-16; lauralkonium chloride; olealkonium chloride; dilauryldimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; polyquaternium-11; polyquaternium-5; polyquaternium-10; polyquaternium-24; cetrimonium chloride; Quaternium-24; mytrimonium chloride; PEG-2 cocomonium chloride; PEG-2 cocoyl quaternium 4; PEG-15 cocoyl quaternium 4; PEG-2 stearyl quaternium 4; and PEG-15 stearyl quaternium 4; PEG-2 oleyl quaternium 4; PEG-15 oleyl quaternium 4, and mixtures thereof.

15. A composition according to claim 1 wherein the silicone surfactant is a dimethicone copolyol with an HLB value of less than 10, and a molecular weight of about 600 to about 20,000.

16. A composition according to claim 1 wherein the silicone surfactant has the formula

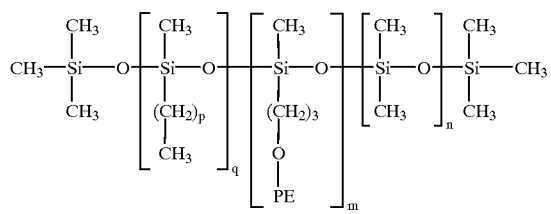

wherein
p is numeral from 7 through 17;
q is a numeral from 1 through 100;
m is a numeral from 1 through 40;
n is a numeral from 0 through 200; and
PE is $(C_2H_4O)_a(C_3H_6O)_b$—H having a molecular weight of about 250 to about 2000, wherein a and b are selected such that the weight ration of $C_2H_4O/C_3H_6O$ is from 100/0 to 20/80.

17. A composition according to claim 16 wherein the silicone surfactant copolyol is cetyl dimethicone copolyol.

18. A composition according to claim 1 wherein said volatile hydrocarbon compound comprises about 6 to 20 carbon atoms.

19. A composition according to claim 1, which comprises a nonvolatile silicone compound selected from the group consisting of a polydimethylsiloxane, polyalkyl siloxane, a polyaryl siloxane and a polyalkylaryl siloxane.

20. A composition in accordance with claim 1 which comprises isoeicosane, isopropyl myristate, or dioctyl adipate.

21. A method for conditioning hair which comprises contacting said hair with a composition according to claim 1.

22. A composition in accordance with claim 1 which further comprises a di- long chain alkyl amine selected from the group consisting of dipalmitylamine, stearamidopropyl dimethylamine, and mixtures thereof.

* * * * *